United States Patent [19]

Koster et al.

[11] 4,195,032

[45] Mar. 25, 1980

[54] PROCESS FOR CONTINUOUSLY WORKING UP SOLUTIONS OF THE TYPE ACCUMULATING IN THE PHOSGENATION OF MONOAMINES

[75] Inventors: Johannes Koster; Peter Heitkämper; Peter Fuhrmann; Helmut Porkert, all of Dormagen, Fed. Rep. of Germany

[73] Assignee: Bayer Aktiengesellschaft, Leverkusen, Fed. Rep. of Germany

[21] Appl. No.: 10,650

[22] Filed: Feb. 9, 1979

[30] Foreign Application Priority Data

Feb. 14, 1978 [DE] Fed. Rep. of Germany ....... 2806214

[51] Int. Cl.$^2$ ................. C07C 118/00; C07C 118/02
[52] U.S. Cl. ...................... 260/453 PH; 260/453 P; 260/453 SP; 203/28
[58] Field of Search ........ 260/453 P, 453 PH, 453 SP

[56] References Cited

U.S. PATENT DOCUMENTS

| | | | |
|---|---|---|---|
| 3,388,145 | 6/1968 | Merz | 260/453 P |
| 3,969,388 | 7/1976 | Urbach et al. | 260/453 P |
| 3,969,389 | 7/1976 | Urbach et al. | 260/453 P |
| 3,991,094 | 11/1976 | Zanker | 260/453 P |
| 4,069,238 | 1/1978 | Zanker | 260/453 P |
| 4,082,787 | 4/1978 | Bassett et al. | 260/453 P |

*Primary Examiner*—Dolph H. Torrence
*Attorney, Agent, or Firm*—Gene Harsh; Joseph C. Gil; R. Brent Olson

[57] ABSTRACT

The present invention relates to an improved process for the continuous production of alkylmonoisocyanates from commercial solutions containing N-alkyl carbamic acid chlorides by thermally decomposing the N-alkyl carbamic acid chlorides in the presence of inert solvents, and recovering the pure monoisocyanates by distillation.

4 Claims, 4 Drawing Figures

PROCESS FOR CONTINUOUSLY WORKING UP SOLUTIONS OF THE TYPE ACCUMULATING IN THE PHOSGENATION OF MONOAMINES

BACKGROUND OF THE INVENTION

It is known that isocyanates can be produced by reacting amines with phosgene. The reaction takes place via a carbamic acid chloride stage, the carbamic acid chlorides decomposing at elevated temperature into the corresponding isocyanates and hydrogen chloride. If the boiling point of the isocyanate to be produced is significantly above the decomposition temperature of the carbamic acid chloride, the hydrogen chloride formed during the decomposition can be removed from the reaction zone without difficulty, particularly where an inert organic solvent is used. If, however, the decomposition temperature of the carbamic acid chloride is close to, or above, the boiling point of the isocyanate, the isocyanate will enter the gas phase where it recombines with the hydrogen chloride to form carbamic acid chloride. Accordingly, decomposition is incomplete and the isocyanate obtained is contaminated with carbamic acid chloride.

The situation as outlined above applies to aliphatic monoisocyanates whose aliphatic radicals contain from 1 to 3 carbon atoms, the difficulties being greatest in the production of methylisocyanate.

Numerous processes which are intended to eliminate the difficulties referred to above are known and described in the art. Numerous publications describe the decomposition of carbamic acid chlorides using hydrogen chloride acceptors.

Thus, it is known that isocyanates can be produced from carbamic acid chlorides in the presence of organic bases (for example, tertiary amines) or carboxylic acid dialkylamides (German Offenlegungsschrift No. 1,593,554) or tetraalkyl ureas (U.S. Pat. No. 3,644,461) in organic solvents. In addition, German Auslegeschrift No. 2,156,761 describes the use of water, and British Pat. No. 1,208,862 describes the use of aqueous solutions or suspensions of inorganic bases, for absorbing the hydrogen chloride. Olefins have also been mentioned as hydrogen chloride acceptors (German Offenlegungschrift No. 2,210,285).

All the processes referred to above have the serious disadvantage that secondary products (corrosive organic or inorganic salts or alkyl chlorides) are formed, which either must be worked up at considerable expense or represent a source of atmospheric pollution. In addition, where organic bases are used, dimeric and trimeric isocyanates can be formed by secondary reactions. In the presence of water, a considerable proportion of the carbamic acid chloride is hydrolyzed to form the corresponding amine hydrochloride.

It is also known that the corresponding N-alkyl carbamic acid esters can be initially produced from the N-alkyl carbamic acid chlorides by reaction with aliphatic or aromatic hydroxyl compounds with the elimination and removal of hydrogen chloride. The isocyanates are subsequently obtained by thermally decomposing these carbamic acid esters (Houben-Weyl, Methoden der Organischen Chemie, Vol. 8, page 126, 1952).

For example, the corresponding monoisocyanates can be liberated by thermal decomposition from N-alkyl carbamic acid-2-hydroxy ethyl esters (U.S. Pat. No. 3,076,007) or from N-alkyl carbamic acid-$\beta$-naphthyl esters (German Offenlegungsschrift No. 2,512,514).

The decomposition products of these processes partially recombine to form the carbamic acid esters upon completion of thermal decomposition. Additionally, non-volatile secondary products accumulate in the high-boiling hydroxyl compounds.

It is also known that low-boiling aliphatic monoisocyanates can be produced directly by the thermal decomposition of carbamic acid chlorides in organic solvents using special processing techniques.

According to German Auslegeschrift No. 1,193,034 and U.S. Pat. No. 3,388,145, thermal decomposition of the carbamic acid chloride is carried out in a reactor provided with a reflux condenser and separation column. Hydrogen chloride escapes through the reflux condenser, while isocyanate, carbamic acid chloride and solvent are retained. The isocyanate which is formed enters the column and can be removed at the head of the column. Most of the isocyanate is returned through a reflux divider so that the carbamic acid chloride ascending into the column passes back into the reactor.

Although this process is eminently suitable for the batch production of alkyl isocyanates, particularly on a laboratory scale, it is nevertheless attended by serious disadvantages which seriously complicate continuous working on a large scale. These disadvantages include the following:

1. Only a small proportion of the isocyanate present in the reactor and in the column can be removed at the head of the column. A large proportion of this isocyanate is removed from the reactor as a sump solution together with the residual non-decomposed carbamic acid chloride. If more product is removed at the head of the column, the product thus removed is not pure monoisocyanate. In that case, it is only possible to obtain mixtures containing considerable proportions of carbamic acid chloride at the head of the column. This disadvantage cannot even be overcome by using columns having a greater separation effect.

2. To obtain isocyanate free from carbamic acid chloride at the head of the column, the column has to be operated with high reflux ratios which involve a high consumption of energy.

3. For decomposing the residual, non-decomposed carbamic acid chloride, the isocyanate-containing carbamic acid chloride solution removed from the sump of the reactor must be returned to the reactor, optionally after part of the solvent has been separated. This inevitably results in a large isocyanate circuit which leads to very low volume-time yields.

4. Another effect of this large isocyanate circuit is that high concentrations of isocyanate are attained in the reactor. In that case, the readily volatile isocyanates are preferentially evaporated when the solutions are heated, so that the product vapors ascending to the reflux condenser have correspondingly high isocyanate contents. The ultimate result of this is that the effectiveness of the thermal removal of hydrogen chloride in the reflux condenser and, hence, the volume-time yield are drastically reduced.

The result of these disadvantages is that, where the above-mentioned process is carried out continuously, the reaction products and the solvent required for decomposing the carbamic acid chlorides have to be repeatedly recycled. The repeated evaporation and condensation of the mixtures, and the need for high reflux ratios in the distillation column of the reactor result in a high energy consumption and in serious losses of yield attributable to the formation of relatively high molecular weight derivatives and secondary products from the isocyanate and carbamic acid chloride (cf. for example H. Ulrich et al, J. Org. Chem. 29, 2401 (1964)).

German Offenlegungsschriften Nos. 2,411,441; 2,411,442; 2,422,211 and 2,503,270 describe process modifications which are also based on the principle of the above-mentioned process.

Thus, German Offenlegungsschrift No. 2,411,441 (corresponding to U.S. Pat. No. 3,969,389) describes a process in which the carbamic acid chloride is partly decomposed into isocyanate and hydrogen chloride by heating the carbamic acid chloride solution under reflux in a reactor equipped with a reflux condenser. The isocyanate thus formed is then isolated in a separate apparatus. The disadvantages referred to above apply to this process as well. In addition considerable outlay on apparatus is necessary.

German Offenlegungsschrift No. 2,411,442 (corresponding to U.S. Pat. No. 3,991,094) describes a process in which, during the thermal decomposition of the carbamic acid chloride under reflux, an inert gas stream is passed through the reaction mixture to remove the hydrogen chloride from the reaction zone. The decomposition of the carbamic acid chloride is accordingly promoted. In actual fact, however, this process does not produce any demonstrable increase in the decomposition of the carbamic acid chloride because the inert gas stream does not have a selective rectifying effect. Thus, not only are increased quantities of hydrogen chloride removed from the reaction zone with the inert gas, but also corresponding increased quantities of low-boiling isocyanate. In addition, the process involves a considerable outlay on apparatus.

The above-mentioned disadvantages also apply to the process described in German Offenlegungsschrift No. 2,503,270. In the first stage of this multistage process, a carbamic acid chloride solution is treated by thermal decomposition under reflux. The solution thus formed is heated again under reflux while an inert gas stream is passed through, the residual carbamic acid chloride being converted into isocyanate.

German Offenlegungsschrift No. 2,422,211 (corresponding to U.S. Pat. No. 3,969,388) describes a process in which the removal of hydrogen chloride from the carbamic acid chloride is carried out by heating the solutions under reflux in 2 to 6 successive reaction zones, followed by isolation of the isocyanate. However, no detectable quantities of hydrogen chloride are eliminated in this process either in the second reaction zone or in the following reaction zones. This could only be achieved by initially isolating isocyanate from the solutions removed from the reaction zones and subsequently introducing the solutions into the following reaction zone.

Finally, U.S. Pat. No. 4,082,787 describes a process whereby a solution of methyl carbamyl chloride in a nonpolar solvent is thermally dehydrochlorinated. The gases formed are condensed at a temperature above the boiling point of methyl isocyanate. Hydrogen chloride gas is removed by condensing the remaining condensable gases at a temperature below the boiling point of methyl isocyanate. The methyl isocyanate is separated from the condensate of the first condensation step.

The object of the instant invention is to provide a process for the continuous processing of commercial solutions containing carbamic acid chloride and recovering the corresponding pure monoisocyanate in high yields, in which undesirably large product circuits, high product losses attributable to the formation of derivative and secondary products and an undesirably high consumption of energy are avoided.

According to the present invention, this object is achieved by the process described in detail in the following.

DESCRIPTION OF THE INVENTION

Figure 1:
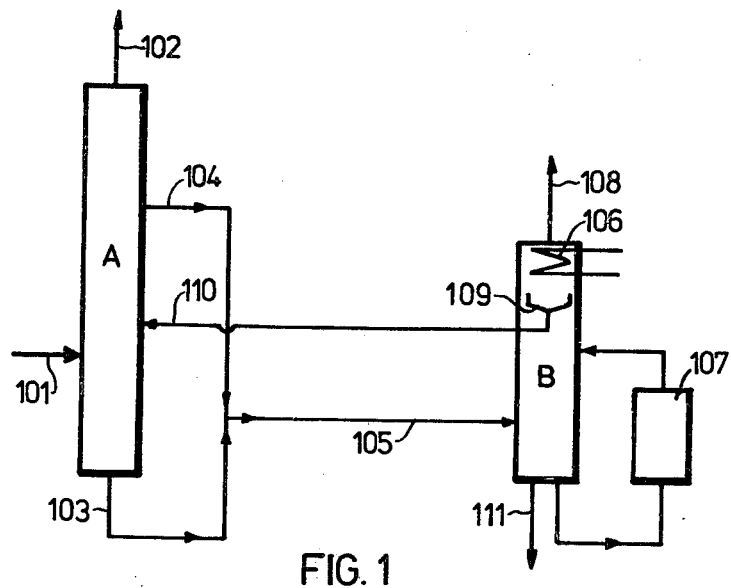
FIGS. 1 through 4 schematically illustrate several embodiments of the instant invention.

The present invention relates to a process for the continuous processing of commercial solutions of the type which accumulate during the phosgenation of monoamines corresponding to the following general formula:

$$R-NH_2$$

wherein
R represents an alkyl radical containing from 1 to 3 carbom atoms which may be unsaturated; and which solutions consist essentially of
(i) carbamic acid chlorides corresponding to the following general formula:

$$R-NH-CO-Cl,$$

(ii) optionally monoisocyanates corresponding to the following general formula:

$$R-NCO$$

wherein
R is defined as above; and
(iii) inert solvents boiling above 80° C. and which boil at least 10° C. above the boiling point of the isocyanate R—NCO, with recovery of the pure monoisocyanate R—NCO, by thermally decomposing the corresponding carbamic acid chloride and distilling the isocyanate thus obtained and the isocyanate already present, if any, characterized in that the solution to be worked up is introduced at any point into a product circuit which has been established
(a) by introducing a solution consisting essentially of the monoisocyanate to be recovered, the carbamic acid chloride to be decomposed and the above-mentioned solvent into a distillation column, in whose head the pure monoisocyanate and in whose sump the solvent, which may be contaminated accumulate, the introduction occurring at a point situated above the column sump;
(b) by removing from the column, at a point situated above the inlet mentioned in (a), a liquid product stream consisting essentially of a concentrated carbamic acid chloride solution, optionally containing monoisocyanate, in the above-mentioned solvent, and combining this product stream with at least part of the sump product obtained in accordance with (a);
(c) by introducing the combined streams obtained in accordance with (b) into a reaction vessel provided with a reflux condenser, or by effecting the combination mentioned in (b) within the above-mentioned reaction vessel, provision being made by heating the streams before and/or after their combination or before and/or after their introduction into the reaction vessel, to ensure that the liquid phase is at least partly evaporated with at least a partial decomposition of the carbamic acid chloride into monoisocyanate and hydrogen chloride; and (d) by allowing the hydrogen chloride formed to escape as a gas above the reflux condenser and, at the same time, returning at least part of the condensate forming in the reflux condenser to the beginning of the circuit according to (a) as the solution to be introduced into the distillation column in accordance with (a), solvent, which may be contaminated, finally being continuously removed at the same time as a liquid from the reaction vessel mentioned in (c).

Starting solutions for the process according to the present invention are commercial solutions of the type which accumulate during the phosgenation of monoamines corresponding to the following general formula:

R—NH₂ wherein
R represents an alkyl radical containing from 1 to 3 carbon atoms, which may be unsaturated. Particularly preferred are those materials where R represents a methyl, ethyl, n-propyl, isopropyl or allyl group, and most preferably a methyl group.

The above-mentioned starting solutions are solutions of the above-mentioned carbamic acid chlorides corresponding to the following general formula:

R—NH—CO—Cl and, optionally, the corresponding monoisocyanates corresponding to the following general formula:

R—NCO in an inert solvent of the type which is used as a reaction medium for the phosgenation reaction or, where phosgenation is carried out in the gas phase, for absorbing the reaction gases, and which generally has a boiling point above 80° C. and at least 10° C. above the boiling point of the monoisocyanate to be produced.

Examples of suitable solvents such as these are n-heptane, n-amyl chloride, 1,2-dichloropropane, isomeric dichlorobutanes, toluene, xylene, ethyl benzene, chlorobenzene, dichlorobenzene, acetic acid butyl ester, and butyric acid ethyl ester. It is, of course, also possible for several solvents to be present in the starting solution. It is preferred, however, to use starting solutions containing chlorobenzene as the solvent.

The commercial starting solutions used for the process according to the present invention contain the above-mentioned carbamic acid chlorides in concentrations of from 0.5 to 40% by weight, preferably in concentrations of from 2 to 15% by weight, and the above-mentioned monoisocyanates, which may optionally be present, in concentrations of from 0 to 30% by weight, and preferably in concentrations of from 0 to 10% by weight.

Commercial starting compounds of the type in question can be produced by conventional processes. They may be obtained, for example, by phosgenating solutions of the corresponding monoamines in the above-mentioned solvents (cf. for example W. Siefken, Liebigs Ann. Chem. 562, (1949)).

The solutions, however, can be obtained very simply by phosgenating the corresponding monoamines in the gas phase and subsequently absorbing the reaction gases formed in the above-mentioned solvents.

To this end, the gaseous monoamine having a temperature of from 0 to 300° C. is reacted with at least one mol per mol of monoamine of gaseous phosgene having a temperature of from 10 to 300° C., optionally in admixture with a dilute inert gas or vaporous solvent. The reaction temperatures are generally in the range of from 240° to 400° C. and preferably in the range of from 300° to 360° C.

A gas-phase reaction such as this is exemplified by the following phosgenation of methylamine: 150 mols per hour of phosgene gas heated to 180° C. are continuously introduced into a standard commercial-grade cylindrical static mixer of the type manufactured by the KENICS company. At the same time, 100 mols per hour of methylamine gas heated to 180° C. are continuously introduced coaxially into the phosgene gas stream directly in front of the static mixer. The dimensions of the static mixer are selected in such a way that the reaction gases flow through the static mixer in a residence time of approximately 0.1 seconds. The reaction temperature is adjusted to 360° C.

The gas-phase phosgenation reactions may, of course, also be carried out by a method other than that described above.

The reaction gases formed during the phosgenation of monoamines in the gas phase are absorbed in the above-mentioned solvents, again by known processes. For example, the upwardly flowing gases may be absorbed in an absorption vessel by the solvents introduced into the vessel above the gas inlet and flowing downwards. The absorption vessel used is most preferably a column which preferably contains additional product coolers for cooling the reaction gases and the solutions formed.

The absorption of the reaction gases in the solvents is preferably carried out in such a way that the hydrogen chloride formed during phosgenation in the gas phase and the excess phosgene optionally present in the reaction gases escape in gaseous form at the upper end of the absorption vessel used (for example, at the head of an absorption column).

The absorption of the above-mentioned reaction gases may, of course, also be carried out in a manner other than that described above.

The solutions formed during the absorption of the reaction gases in the above-mentioned solvents may also contain phosgene. The concentrations of phosgene in these solutions are dependent inter alia upon the excess of phosgene used for phosgenation in the gas phase, upon the solvents used and upon the method by which the reaction gases are absorbed in the solvents. Accordingly, the concentrations of phosgene in these solutions may fluctuate over a wide range.

Known methods can be used for freeing these solutions from the phosgene which may be present in them. Thus, the above-mentioned separation of phosgene from these solutions may be carried out, for example, by fractional distillation in a separation column.

The liquid phosgene-free mixtures obtained are essentially solutions of the above-mentioned carbamic acid chlorides in the above-mentioned solvents. They may also contain the above-mentioned monoisocyanates, the formation of which may have various causes. For example, the hot reaction gases formed during phosgenation in the gas phase contain isocyanates which, during subsequent absorption in a solvent, recombine with hydrogen chloride, in some cases only incompletely. In addition, isocyanates for example may be formed by the thermal elimination of hydrogen chloride from the corresponding carbamic acid chlorides when the parent monoamines are phosgenated under reflux in a solvent or when solutions containing carbamic acid chlorides are heated for liberating dissolved phosgene. The concentrations of monoisocyanate in these solutions are dependent inter alia upon the type of monoamine used for phosgenation, upon the type of solvents used, upon the dilution of the solutions with the above-mentioned solvents, upon the method used for absorbing the reaction gases and upon the method used for the separation of dissolved phosgene.

In the process according to the present invention, the solutions which may already contain monoisocyanate in the above-mentioned concentrations may be used without further working up. It is also possible, however, to remove the monoisocyanate present in the solutions in a separate distillation step in order to use solutions containing almost exclusively carbamic acid chloride in the process according to the present invention. A procedure such as this, however, would be attended by the problem of selectively removing the monoisocyanate by distillation, so that the process according to the present invention is generally not preceded by any such superfluous separation of the monoisocyanate already present.

The principal observation on which the process according to the present invention for working up the above-mentioned commercial solutions is based, lies in the fact that the required monoisocyanate can be obtained in optimal yields and purity from a mixture consisting essentially of monoisocyanate, carbamic acid chloride and solvent. This is achieved by thermally decomposing the carbamic acid chloride into isocyanate and hydrogen chloride, followed by working up by distillation. The mixture in question is continuously introduced laterally into a distillation column, the pure monoisocyanate being removed overhead, a side stream consisting essentially of concentrated carbamic acid chloride solution being simultaneously removed from the column at a point situated above the above-mentioned inlet, the side stream thus removed being combined with at least part of the solvent, which may be contaminated with carbamic acid chloride, which accumulates in the sump of the column. The combined streams are delivered to a separator where they are separated into hydrogen chloride, solvent and solution containing monoisocyanate, carbamic acid chloride and solvent to be returned to the column.

Accordingly, the described system is a circuit from which pure isocyanate is removed at the head of the column while hydrogen chloride and solvent are removed in the separator. For carrying out the continuous process according to the present invention, it is sufficient to deliver the commercial solution to be worked up to this circuit at any point thereof in a quantity which corresponds to the quantity of monoisocyanate, hydrogen chloride and solvent accumulating.

Although it is known that three-component mixtures can be separated up by fractional column distillation in such a way that the lowest-boiling product is recovered at the head of the column, the high-boiling product from the sump of the column and the middle-boiling product from a side stream, a distillation process such as this with side stream removal generally leads to a reduction in the yield of the lowest-boiling head product. This is because some of the head product is always removed with the middle-boiling product in the side stream. Accordingly, it must be regarded as extremely surprising that, in the process according to the present invention, a maximum yield of head product (monoisocyanate) is only possible when, as described above, a side stream is removed, combined with the sump, and the combined streams further treated.

The yields of monoisocyanate obtained by the process according to the present invention carried out in this way are considerably higher than those which would be obtained by simple distillation, i.e. without side stream removal.

The process according to the present invention is described in more detail with reference to the accompanying drawings. The apparatus illustrated in FIGS. 1 to 4 are merely examples of apparatus suitable for carrying out the process according to the present invention. The process according to the present invention is not, however, confined to the use of the apparatus illustrated in FIGS. 1 to 4.

In FIG. 1, (A) is a distillation column and (B) a splitter which consists essentially of (i) a reaction vessel heatable by a circulation evaporator (107) and surmounted by a reflux condenser (106), and (ii) a removal tray arranged below the reflux condenser for the condensate (109).

In a first embodiment of the process according to the present invention, the apparatus shown in FIG. 1 is used. The commercial solution (101) to be worked up is introduced into the distillation column (A), in whose head the pure monoisocyanate (102), and, in whose sump, the optionally contaminated solvent (103) accumulate. A side stream (104) is removed above the inlet for the solutions (101), being combined with the solvent (103) removed from the sump. The combined streams (105) are introduced into the reaction vessel (B) which is provided with a coil condenser as reflux condenser (106) and in which they are heated by means of the circulation evaporator (107). The hydrogen chloride formed (108) escapes above the reflux condenser (106), while condensate forming on the reflux condenser (106) is removed from the reaction vessel (B) on a removal tray (109) and returned to the distillation column (A) as a solution (110) containing monoisocyanate, carbamic acid chloride and solvent. At the same time, possibly contaminated solvent (111) is removed as liquid from the reaction vessel (B).

Figure 2:
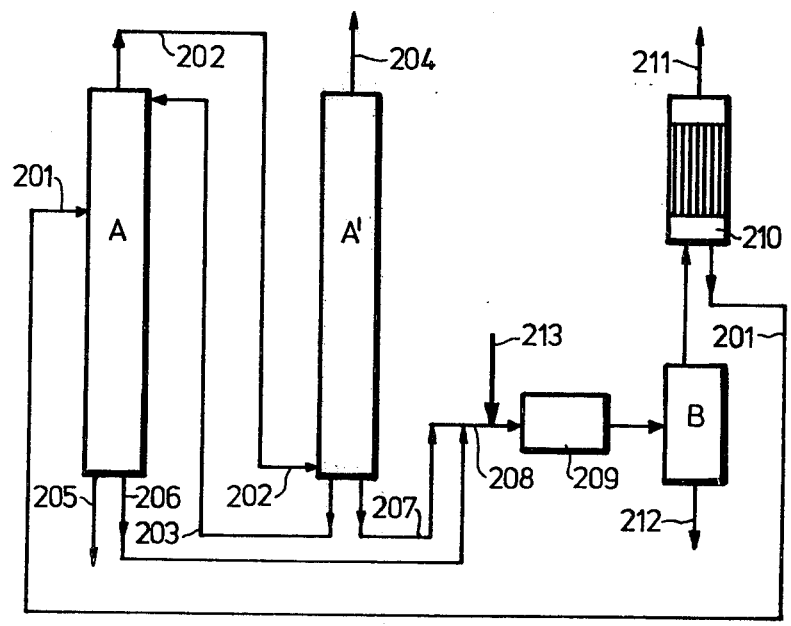

In FIG. 2, (A) is a distillation column, (A') is another distillation column arranged in series with the distillation column (A), and (B) is a splitter which is heatable by a straight-flow heater (209) and which is connected to a reflux condenser (210).

In a second possible embodiment of the process according to the present invention, the apparatus shown in FIG. 2 is used. The condensate (201) containing monoisocyanate, carbamic acid chloride and solvent which accumulates in the reflux condenser (210) arranged above the splitter (B) is introduced into the upper part of the distillation column (A). This is connected to a second column (A′) in such a way that the mode of operation of the combined columns (A) and (A′) corresponds to the mode of operation of the single column illustrated in FIG. 1. Accordingly, the vapors (202) accumulating at the head of the column (A) are introduced into the lower part of the column (A′). The sump solution (203) of the column (A′) is correspondingly returned to the head of the column (A). The pure monoisocyanate accumulates in the head of the column (A′), and the possibly contaminated solvent streams (205) and (206) accumulate in the sump of the column (A). A product stream (207), which may be regarded as a side stream of the distillation unit consisting of columns (A) and (A′), is removed from the sump of the column (A′). This side stream is combined with the component sump stream (206) which may contain from 20 to 100% of the total sump product of the column (A). The combined streams (208) are heated with the commercial solution (213) to be worked up in accordance with the present invention in the straight-flow heater (209), with at least partial evaporation, and introduced into the reaction vessel (B) provided with a multiple tube condenser as reflux condenser (210). The hydrogen chloride formed (211) escapes above the reflux condenser (210) while the condensate accumulating in the reflux condenser is returned as stream (201) to column (A). At the same time, possibly contaminated solvent (212) is removed as liquid from the reaction vessel (B).

Figure 3:
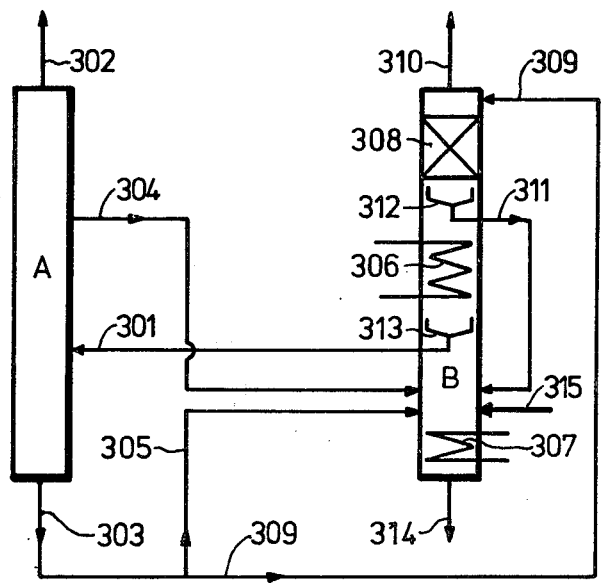

In FIG. 3, (A) is a distillation column and (B) is a splitter which is heatable by means of a heater (307) and which contains a built-in reflux condenser (306), a built-in tower packing (308), a built-in "washing solution removal tray" (312) and a removal tray (313) for the condensate of the reflux condenser.

A third possible embodiment of the process according to the present invention is carried out in the apparatus shown in FIG. 3. The condensate (301) containing monoisocyanate, carbamic acid chloride and solvent which is formed in the reflux condenser (306) and which collects in the removal tray (313) is introduced into the distillation column (A), in whose head the pure monoisocyanate (302) and in whose sump the possibly still contaminated solvent (303) accumulate. A side stream (304) is removed at a point situated above the inlet for the solution (301). This side stream (304) together with a part (305) of the solvent (303) removed from the sump of column (A) and the commercial solution (315) to be worked up are introduced into the heatable splitter (B), combined and heated by means of the heater (307) with partial evaporation and partial decomposition of the carbamic acid chloride. The hydrogen chloride escaping above the reflux condenser (306) is washed in the tower packing (307) with another part (309) of the solvent (303) removed from the sump of column (A) and escapes from the splitter (B) is substantially pure form (310). The washing solution formed (311) is introduced via a removal tray (312) into the lower part of the reaction vessel. The condensate forming in the reflux condenser (306) is removed from the reaction vessel through a removal tray (313) and returned to the distillation column (A). At the same time, possibly contaminated solvent (314) is removed as liquid from the reaction vessel, i.e. from the splitter (B).

Figure 4:
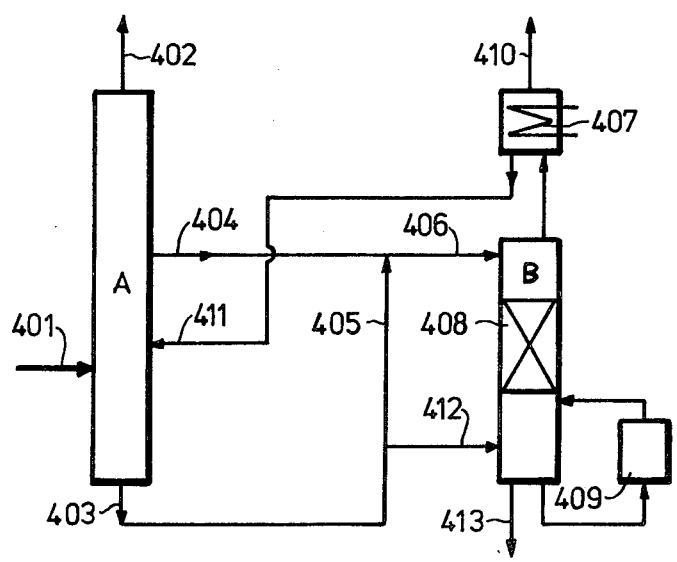

In FIG. 4, (A) is a distillation column and (B) is a splitter which is heatable by means of a circulation evaporator (409), has a tower packing (408) and is connected to a reflux condenser (407).

In a fourth possible embodiment, the process according to the present invention is carried out in the apparatus illustrated in FIG. 4. The commercial solution (401) to be worked up is introduced, as in the first embodiment, into the distillation column (A) in whose head the pure monoisocyanate (402) and in whose sump the possibly contaminated solvent (403) accumulate. A side stream (404) is removed at a point situated above the inlet for the solution (401) and combined with a part (405) of the solvent (403) removed from the sump of the column (A). The combined streams (406) are introduced into the reaction vessel (B) which is provided with a coil condenser as reflux condenser (407) and which comprises a separation-active tower packing (408) below the point at which these streams are introduced. The sump liquid of the reaction vessel (B) is heated by means of a circulation evaporator (409). The hydrogen chloride formed (410) escapes above the reflux condenser (407). The condensate containing monoisocyanate, carbamic acid chloride and solvent which forms in the reflux condenser (407) is returned to column (A) at point (411). Another part (412) of the solvent (403) removed from the sump of the column (A) is introduced into the sump of reaction vessel (B). At the same time, possibly contaminated solvent (413) is removed as liquid from the reaction vessel (B).

One feature which is common to all the embodiments of the process according to the present invention, because it is essential to the invention, is the removal of a side stream above the point of entry into the distillation column, the combination of this side stream with at least part of the solvent accumulating in the sump of the distillation column, the at least partial division of the combined streams into solvent, hydrogen chloride and condensate to be returned to the column, and the introduction of the commercial solution to be worked up any point of this circuit. In the practical application of the process according to the present invention, it does not matter whether the commercial solutions to be worked up at which accumulate during the phosgenation of the above-mentioned monoamines, are introduced into the distillation column or into the reaction vessel (or separator). Their introduction, however, is best gauged according to the composition of the starting solutions which can fluctuate over a wide range. Thus, it is advantageous to introduce solutions having a high content of monoisocyanates into the distillation column, whereas solutions having a low content of monoisocyanates are best introduced into the reaction vessel.

In all the embodiments of the process according to the present invention, the ratio by weight of the commercial solution to be worked up in accordance with the invention, which is introduced into the circuit, and the quantity of product present in the circuit is from 1:0.1 to 1:20 and preferably from 1:0.2 to 1:10.

The stream returned from the reflux condenser to the column generally contains from 1 to 30% by weight, and preferably from 3 to 20% by weight, of monoisocyanate and from 0.5 to 30% by weight, preferably from 2 to 25% by weight, of carbamic acid chloride.

The side stream removed from the column generally contains from 0.1 to 20% by weight, preferably from 0.2 to 10% by weight, of monoisocyanate and from 20 to 80% by weight, preferably from 30 to 65% by weight, of carbamic acid chloride.

The solvent accumulating in the sump of the distillation column contains from 0 to 3% by weight, preferably from 0 to 1% by weight, of carbamic acid chloride and from 0 to 3% by weight, preferably from 0 to 1% by weight, of monoisocyanate.

As already mentioned in the description of the second, third and fourth embodiment of the process according to the present invention, there is no need for the total quantity of sump product to be mixed with the side stream. It is generally sufficient to use only that proportion of sump product for remixing with the side stream which is required for adjusting a carbamic acid chloride content of from 1 to 30% by weight and preferably from 3 to 25% by weight in the combined solution.

The solvent removed in a liquid form from the reaction vessel or splitter generally contains from 0 to 3% by weight, preferably from 0 to 1% by weight, of carbamic acid chloride and from 0 to 3% by weight, preferably from 0 to 1% by weight, of monoisocyanate.

The proportion of solvent accumulating as sump product of the distillation column which is not required for remixing with the side stream may either be used as washing liquid for the hydrogen chloride leaving the reflux condenser, as mentioned in the description of the third embodiment, or delivered to the sump of the divider (fourth embodiment). It is also possible to remove from the system part of the solvent accumulating from the sump of the column, as mentioned in the description of the second embodiment.

The solvents which may be contaminated with monoisocyanate and/or carbamic acid chloride in the practical application of the process may be advantageously purified by distillation, for example, in a stripping column. In this case, the purified solvents and, monoisocyanates and/or carbamic acid chlorides, optionally in admixture with solvent, are recovered. The last-mentioned distillation products are best introduced into the reaction vessel or into the distillation column. The solvents accumulating in the process according to the invention may also be used after purification, or even without purification, as starting solvents for the production of the commercial solutions to be worked up in accordance with the invention.

The process according to the present invention is not limited to the embodiments described by way of example. Thus, it is also possible, as mentioned in the description of the second embodiment, to use several columns for working up by distillation providing they are arranged one behind the other in such a way that their technical function corresponds to the function of a single column.

The removal of the side stream from the distillation column is effected "above" the point at which the starting solutions are introduced. This means that in cases where several interconnected columns are used, the side stream in question is removed in line with the separation effect between the inlet for the solution returned from the splitter and, optionally, for the starting solution and the outlet for the pure monoisocyanate.

The process according to the present invention can be carried out in apparatus known in chemical technology.

Known coil condensers or multiple-tube condensers may, for example, be used as the reflux condensers.

Also, known straight-flow heaters may be used for heating the product streams introduced into the reaction vessel (splitter). The liquids may even be heated, for example, inside the reaction vessel by means of jacket heaters, insertion-type evaporators or circulation evaporators arranged at the bottom end of the reaction vessel.

Any of the vessels commonly used in chemical technology may be used as the reaction vessel. For carrying out the process according to the present invention, it is not essential to arrange the reflux condenser in the reaction vessel or splitter. Instead, the reflux condenser may even be connected to the reaction vessel through corresponding pipes. It can be particularly advantageous to use separation columns as the reaction vessel. In this case, the elimination and separation of hydrogen chloride and the purification of the solvent used by fractional distillation can be carried out simultaneously in one apparatus (cf. fourth embodiment).

The removal of at least part of the condensate forming in the reflux condenser is carried out by known methods, for example, by means of a removal tray arranged below the reflux condenser. In cases where a reflux condenser arranged outside the reaction vessel is used, the condensate may even be collected, for example, at the bottom of this condenser and removed there.

Known apparatus for the side stream removal may be used.

In carrying out the process according to the present invention, all the apparatus used may be operated under reduced pressure, at normal pressure and also under excess pressure. In general, a pressure of from 0.01 to 10 bars prevails in the apparatus. The pressure conditions are, of course, dependent upon the temperature and the volatility of the individual components.

The temperature prevailing in the splitter is generally from 30° C. to 250° C. and preferably from 80° C. to 160° C. In general, the temperature is gauged in such a way that from 5 to 95%, preferably from 10 to 65%, of the liquid introduced evaporates with at least partial decomposition of the carbamic acid chloride.

In carrying out the process according to the present invention, the main distillation column is generally operated with a reflux ratio of from 1:1 to 1:30.

The process according to the present invention has the following particular advantages over conventional processes:

1. No additional substances, such as hydrogen chloride acceptors or hydroxyl compounds, are required for carrying out the process. Accordingly, no separate reaction steps are required for carrying out the process, nor do any secondary or derivative product, requiring special working up accumulate.

2. The process according to the invention can be carried out using apparatus which are known and commonly used in the art, for example, columns and heat exchangers. Complicated apparatus which are difficult to manufacture are not required for this purpose. In particular, the removal of a side stream from the distillation column, which is essential to the invention, may be carried out using conventional methods of the prior art.

3. The principle according to the invention of removing a side stream and recombining the streams, which is simple to put in practice, also provides for a much more effective recovery of the monoisocyanates and for a much more effective elimination of hydrogen chloride from the carbamic acid chlorides, so that far fewer product circuits are required for recovering the monoisocyanates. The result of this is that the specific energy consumption is significantly lower and the volume-time yield of production is considerably increased.

4. By virtue of the low reflux ratios in the distillation column and the small number of product circuits, the heat-sensitive monoisocyanates and carbamic acid chlorides are subjected to far less thermal stress in the process according to the invention. As a result, only very small fractions of these substances are reacted to form secondary products so that the monoisocyanates can be obtained in substantially quantitative yields.

5. By virtue of the process according to the invention, it is possible, if desired, to carry out simultaneously the removal of hydrogen chloride and the purification of solvent in one apparatus. This saves both investment costs and also energy costs (cf. fourth embodiment).

The alkyl monoisocyanates obtainable by the process according to the present invention are valuable starting compounds for plant protection agents and pharmaceutical products.

A packed column which is 6 meters tall (diameter of the lower 2 meters: 100 mm, diameter of the upper 4 meters: 80 mm), and which is heatable by means of a circulation evaporator was used for each of the following Examples. The column was operated with a reflux ratio of 1:8. In each case, the inlets were situated at a height of 2 meters, while the side stream was removed at a height of 3 meters.

All the percentages quoted represent % by weight.

EXAMPLES

EXAMPLE 1 (FIG. 1)

A commerical solution of 2.01% of methylisocyanate and 6.33% of methyl carbamic acid chloride in chlorobenzene is continuously worked up. 48.96 kg/h of this solution are introduced into the distillation column (A) (sump temperature 136° C./1.2 bars) at (101), 2.74 kg/h of pure methyl isocyanate (102) being removed at the head of this column and 98.35 kg/h of product (0% methylisocyanate; 0.39% of methyl carbamic acid chloride) from its sump (103). 18.43 kg/h of solution (6.09% of methylisocyanate; 51.73% of methyl carbamic acid chloride) are removed as the side stream (104) and combined with the sump product (103). The combined streams (116.8 kg/h; 0.96% of methylisocyanate; 8.50% of methyl carbamic acid chloride) are introduced into the reaction vessel resp.splitter (B) at (105) and partially evaporated by heating to 128° C./1.0 bar. 1.17 kg/h of hydrogen chloride (108) escape above the reflux condenser (106). 70.56 kg/h of condensate (4.07% of methyl isocyanate; 9.67% of methyl carbamic acid chloride) are removed via the removal tray (109) and introduced into the distillation column (A) at (110). 45.05 kg/h of liquid (0.18% of methylisocyanate; 0.20% of methyl carbamic acid chloride) are removed from the sump of the reaction vessel (B) at (111). EXAMPLE 2 (FIG. 3)

A commercial solution of 0.41% of methylisocyanate and 7.32% of methyl carbamic acid chloride in chlorobenzene is continuously worked up. 67.70 kg/h of this solution are introduced into, and partially evaporated in, the reaction vessel (B). 88.30 kg/h of condensate (4.07% of methylisocyanate; 9.57% of methyl carbamic acid chloride) are removed via the removal tray (313) and introduced into the distillation column (A) (sump temperature: 135° C./1.2 bars) at (301). 2.79 kg/h of pure methylisocyanate (302) are removed from the head of the column, 70.55 kg/h of liquid (0% of methylisocyanate; 0.99% of methyl carbamic acid chloride) are removed from the sump (303) of the column and 14.96 kg/h of solution (5.35% of methylisocyanate; 51.82% of methyl carbamic acid chloride) are recovered through the side stream (304). The side stream (304) and 56.69 kg/h of the sump product (303) removed from the column (305) are introduced into the lower part of the reaction vessel (B) and partially evaporated at 130° C./1.1 bar. The gas stream escaping above the reflux condenser (306) is washed with 13.86 kg/h of liquid sump product from column (A) in the tower packing (308), the liquid sump product being introduced into the reaction vessel (309) above the packing (308). The washing solution running off (14.43 kg/h; 0% of methylisocyanate; 4.88% of methyl carbamic acid chloride) is introduced through the removal tray (312) into the lower part of the reaction vessel (B) at (311). 1.78 kg/h of hydrogen chloride gas (310) escape at the head of the reaction vessel. 63.12 kg/h of liquid (0.44% of methylisocyanate; 0.60% of methyl carbamic acid chloride) are removed at the base of the reaction vessel (314).

EXAMPLE 3 (FIG. 4)

A commerical solution of 2.70% of methylisocyanate and 8.72% of methyl carbamic acid chloride in chlorobenzene is continuously worked up. 36.64 kg/h of this solution are introduced at (401) into the distillation column (A) (sump temperature: 136° C./1.2 bars), at whose head 2.91 kg/h of pure methyl isocyanate (402) and at whose sump (403) 55.81 kg/h of product (0% of methylisocyanate; 0.66% of methyl carbamic acid chloride) are obtained. 18.12 kg/h of solution (5.62% of methylisocyanate; 50.90% of methyl carbamic acid chloride) are removed from the column as a side stream (404) and combined with 27.91 kg/h of the sump product of the column (405). The combined liquids (46.03 kg/h; 2.21% of methylisocyanate; 20.43% of methyl carbamic acid chloride) are introduced into the reaction vessel (B) at a point (406) situated above the packing (408) and partially evaporated therein. The necessary heat is provided by the solvent vapors ascending through the pack (408) which in turn are obtained by heating the sump of the reaction vessel at 135° C./1.1 bars by means of the circulation evaporator (409). 1.23 kg/h of hydrogen chloride gas (410) escape above the reflux condenser (407). The condensate (40.19 kg/h; 7.31% of methylisocyanate; 15.90% of methyl carbamic acid chloride) running off from the reflux condenser (407) is returned to the distillation column (A) at (411). 27.90 kg/h of the sump product (403) removed from the distillation column (A) are introduced at (412) into the sump of the reaction vessel (B) from which 32.51 kg/h of liquid (0% of methylisocyanate; 0.15% of methyl carbamic acid chloride) are removed at (413).

EXAMPLE 4 (FIG. 4)

A commerical solution of 6.07% of ethylisocyanate and 4.03% of ethyl carbamic acid chloride in chlorobenzene is continuously worked up. 33.62 kg/h of this solution are introduced at (401) into the distillation column (A) (sump temperature: 136° C./1.2 bars), at whose head 2.91 kg/h of pure ethylisocyanate (402) and at whose sump (403) 42.83 kg/h of product (0% of ethylisocyanate; 0.17% of ethyl carbamic acid chloride) are obtained. 7.68 kg/h of solution (18.21% of ethylisocyanate; 31.58% of ethyl carbamic acid chloride) are removed from the column as a side stream (404) and combined with 10.71 kg/h of the sump product of the column (405). The combined liquids (18.39 kg/h; 7.61% of ethylisocyanate; 13.30% of ethyl carbamic acid chloride) are introduced into the reaction vessel (B) (sump temperature: 136° C./1.1 bars) at a point (406) situated above the packing (408) and are partially evaporated therein. 0.45 kg/h of hydrogen chloride gas (410) escape above the reflux condenser (407). The condensate (19.80 kg/h; 11.48% of ethylisocyanate; 5.79% of ethyl carbamic acid chloride) running off from the reflux condenser (407) is returned to the distillation column (A) at (411). 32.12 kg/h of the sump product (403) removed from the distillation column (A) are introduced at (412) into the sump of the reaction vessel (B) from which 30.26 kg/h of liquid (0% of ethylisocyanate; 0.09% of ethyl carbamic acid chloride) are removed at (413).

What is claimed is:

1. A process for continuously working up solutions of the type which accumulate during the phosgenation of monoamines corresponding to the following general formula:

$$R-NH_2$$

wherein
R represents an alkyl radical containing from 1 to 3 carbon atoms which may be unsaturated; and which solutions consist essentially of carbamic acid chlorides corresponding to the following general formula:

$$R-NH-CO-Cl,$$

optionally monoisocyanates corresponding to the following general formula:

$$R-NCO,$$

wherein
R is defined as above;
and inert solvents boiling above 80° C. and at least 10° C. above the boiling point of the isocyanate R—NCO, with recovery of the pure monoisocyanate R—NCO by thermally decomposing the corresponding carbamic acid chloride and distilling the isocyanate obtained and the isocyanate already present, if any, characterized in that the solution to be worked up is introduced to any point into a product circuit which has been established
(a) by introducing a solution consisting essentially of the monoisocyanate to be recovered, the carbamic acid chloride to be decomposed and the above-mentioned solvent into a distillation column, in whose head the pure monoisocyanate and in whose sump the solvent, which may be contaminated, accumulate, at a point situated above the column sump;
(b) by removing from the column, at a point situated above the inlet mentioned in (a), a liquid product stream consisting essentially of a concentrated carbamic acid chloride solution, optionally containing monoisocyanate, in the above-mentioned solvents, and combining this product stream with at least part of the sump product obtained in accordance with (a);
(c) by introducing the combined streams obtained in accordance with (b) into a reaction vessel provided with a reflux condenser, or by effecting the combination mentioned in (b) within the above-mentioned reaction vessel, provision being made by heating the streams before and/or after their combination or before and/or after their introduction into the reaction vessel, to ensure that the liquid phase is at least partly evaporated with at least a partial decomposition of the carbamic acid chloride into monoisocyanate and hydrogen chloride; and
(d) by allowing the hydrogen chloride formed to escape as a gas above the reflux condenser and, at the same time, returning at least part of the condensate forming in the reflux condenser to the beginning of the circuit according to (a) as the solution to be introduced into the distillation column in accordance with (a), solvent, which may be contaminated, being continuously removed at the same time as a liquid from the reaction vessel mentioned in (c).

2. A process as claimed in claim 1, characterized in that the solution to be continuously worked up is introduced at the same point as, or at a different point from, the solution to be introduced into the distillation column in accordance with (a) into the same distillation column above its sump and below the point at which the side stream is removed in accordance with (b).

3. A process as claimed in claim 1, characterized in that the commercial solution to be worked up is introduced into the reaction vessel optionally after admixture with a stream to be introduced into the reaction vessel.

4. A process as claimed in claim 1, characterized in that solutions of the type accumulating during the phosgenation of methylamine are used as the solutions to be worked up.

* * * * *